United States Patent [19]

Raynor et al.

[11] Patent Number: 4,904,714
[45] Date of Patent: Feb. 27, 1990

[54] SYNTHETIC RESIN COMPOSITION AND ITS METHOD OF USE

[75] Inventors: Robert J. Raynor, North Branford; Francis W. Migliaro, Jr., Waterbury, both of Conn.

[73] Assignee: Olin Corporation, Cheshire, Conn.

[21] Appl. No.: 279,697

[22] Filed: Dec. 5, 1988

Related U.S. Application Data

[60] Division of Ser. No. 105,356, Oct. 2, 1987, Pat. No. 4,816,585, and a continuation-in-part of Ser. No. 22,311, Mar. 5, 1987, abandoned.

[51] Int. Cl.⁴ .................. C08J 5/34; C07D 401/04
[52] U.S. Cl. ............................ 524/100; 544/296; 544/310; 544/312; 540/186; 540/191; 540/223; 546/224; 546/244
[58] Field of Search ............................ 524/100

[56] References Cited

U.S. PATENT DOCUMENTS

| | | | |
|---|---|---|---|
| 3,297,699 | 1/1967 | Schmidt et al. | 544/310 |
| 3,941,744 | 3/1976 | Murayama et al. | 260/45.8 |
| 4,038,277 | 7/1977 | Habermeier et al. | 544/269 |
| 4,066,615 | 1/1978 | Murayama et al. | 260/45.8 |
| 4,097,587 | 6/1978 | Soma et al. | 260/45.8 |
| 4,144,344 | 3/1979 | Eichenberger et al. | 544/296 |
| 4,241,208 | 12/1980 | Murayama et al. | 546/20 |
| 4,329,460 | 5/1982 | Miyashita et al. | 544/301 |
| 4,414,216 | 11/1983 | Kawakita et al. | 524/102 |
| 4,499,220 | 2/1985 | Minagawa et al. | 544/312 |
| 4,514,403 | 4/1985 | Tashiro et al. | 544/312 |
| 4,548,973 | 10/1985 | Raynor | 546/102 |
| 4,816,507 | 3/1989 | Cantatore et al. | 524/100 |

FOREIGN PATENT DOCUMENTS

| | | |
|---|---|---|
| 0047990 | 3/1982 | European Pat. Off. |
| 0068331 | 1/1983 | European Pat. Off. |

*Primary Examiner*—Richard L. Raymond
*Assistant Examiner*—James H. Turnipseed
*Attorney, Agent, or Firm*—Dale Lynn Carlson

[57] ABSTRACT

Tetraalkylpiperidinyl substituted uracil derivatives are disclosed which can be represented by the formula

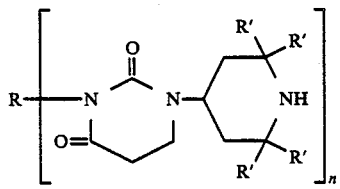

wherein each R' is independently an alkyl radical, n is 1 or 2 and R is a substituted or unsubstituted aliphatic radical, cycloaliphatic radical, aromatic radical or aromatic-aliphatic radical.

These derivatives are useful as UV light stabilizers in synthetic resins.

14 Claims, No Drawings

SYNTHETIC RESIN COMPOSITION AND ITS METHOD OF USE

This is a division of application Ser. No. 105,356, filed Oct. 2, 1987, now Pat. No. 4,816,585 which is a continuation-in-part application of U.S. application Ser. No. 022,311, filed Mar. 5, 1987, now abandoned, and assigned to the assignee of the present application.

This invention relates to certain uracil derivatives and their use as ultraviolet light stabilizers.

It is well known that the physical properties of various synthetic resins deteriorate as a result of extended exposure to ultraviolet (UV) light. This deterioration, which varies in degree and nature depending on the particular polymer structure and on the location and duration of the exposure, has been attributed at least in part to a free radical generating photooxidation reaction. The free radicals so formed will attack the polymer chain to form additional free radicals by a self-propagating mechanism. Manifestations of the degradative effect of UV light on such polymers as polyethylene, polypropylene, and polyvinyl chloride include loss of mechanical strength (e.g., reduced tensile strength and flexibility), discoloration, cracking, and dimensional or surface change.

Over the years, substantial research and development work has been carried out in search of additives which, when incorporated in the resin, would have the effect of preventing, or stabilizing the resin against, photodegradation. As a result, numerous materials have been developed or identified for use as UV stabilizer additives.

Depending on the chemistry of the particular additive, its function as a UV stabilizer may fall in one of several categories. For example, the additive may serve as a screener, preventing the light from impacting on the plastic's molecular structure, or as a preferential absorber of UV light. A third category of UV light stabilizers is that of the so-called "scavengers". The hindered amines (e.g., tetramethyl piperidine) are generally known to serve that function. They trap and transform to a harmless species the free radicals formed as a result of the initial photo-oxidation of the plastic thus interrupting the propagation stage of the photodegradation process. The uracil compounds of this invention fall in this category of UV light stabilizers.

It is also generally well-known in the art that UV stabilizers must meet certain criteria if they are to be useful as additives in plastics. Compatability with, and retention in, the resin or plastic in which the additive is to be used are among the more important requirements. The stabilizer also should impart little or no color to the resin.

Considering the high temperatures at which plastics are processed, it is also important in certain applications that the UV stabilizer be non-volatile and thermally stable at high temperatures. For the most part, only prior art UV stabilizers of the polymeric type can meet this requirement.

Now, in accordance with the invention, new, non-polymeric uracil derivatives have been found which meet the foregoing criteria. Further according to the invention, synthetic resin compositions are stabilized against photodegradation by the inclusion therein of the novel uracil derivatives disclosed herein.

The uracil derivatives of the invention are pyrimidinediones which can be represented by the formula

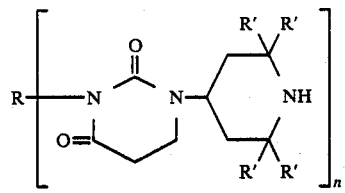

I wherein each R' is independently an alkyl radical, n is 1 or 2, and R is a substituted or unsubstituted aliphatic radical, cycloaliphatic radical, aromatic radical or aromatic-aliphatic radical.

The preferred uracil compounds of the invention are the tetramethylpiperidinyl substituted uracil derivatives which can be represented by formula II as follows

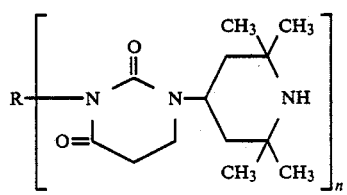

II wherein n and R are as defined above. Particularly preferred are compounds of formula II in which n is 2. These compounds have been found to have suprisingly high thermal stability. Also particularly preferred are those compounds of formula II in which R is an unsubstituted radical selected from the group consisting of alkylene having 1 to 12, more preferably 3 to 10, carbon atoms, cycloalkylene having 5 to 20, more preferably 6 to 15, carbon atoms, arylene having 6 or 12 ring carbon atoms, aralkylene having 7 to 20, more preferably 7 to 16, carbon atoms, and alkarylene having 7 to 20, more preferably 7 to 16, carbon atoms.

The uracil derivatives represented by formula II above can be prepared by a multi-step process using readily available raw materials. The first step involves the reaction of 4-amino-2,2,6,6-tetra methylpiperidine with methyl acrylate to form N-(2,2,6,6-tetramethylpiperidin-4-yl)-amino-3-propionic acid methyl ester. This reaction, which is carried out at ambient or higher temperatures and in the presence of an appropriate solvent, takes about 2 to 48 hours to be complete depending on the temperature. It is illustrated by equation A below

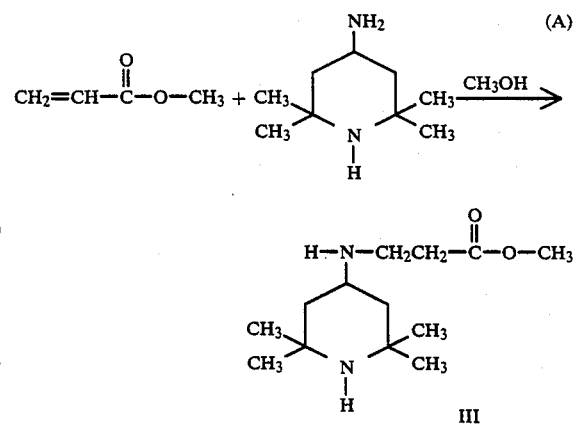

The resulting N-(2,2,6,6-tetramethylpiperidin-4-yl)-amino-3-propionic acid methyl ester, compound III, is then recovered by distilling off the solvent.

The next step in the preparation of the uracil derivatives of the invention is the reaction of compound III with an organic mono- or diisocyanate as depicted by the following equation B in which R and n are defined above

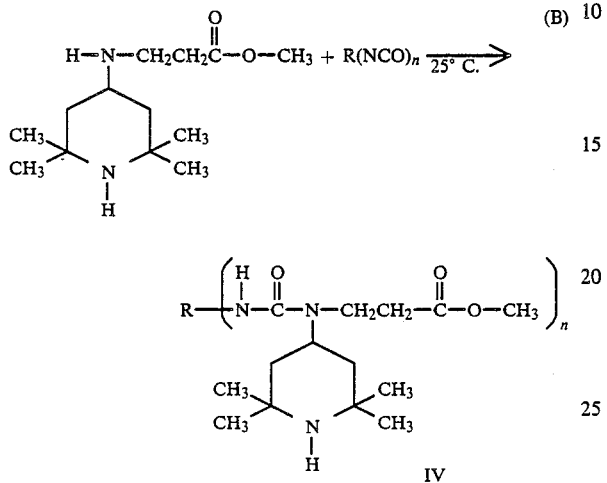

In carrying out the reaction, a solution of the organic isocyanate, in an inert solvent such as an appropriate ether or methylene chloride, is added slowly to a continuously agitated solution of compound III. The reaction being exothermic, the temperature of the reaction mixture is maintained at about 25° C. by means of an ice bath. After the addition is completed, stirring of the reaction mixture is continued for some time, i.e., about 1-2 hours, while maintaining the temperature at 25° C. Then the mixture is refluxed. The resulting urea product, compound IV, is then separated by filtration, washed with solvent and dried in a vacuum oven.

The final step in the preparation of the uracil compounds of the invention is the cyclization of the urea, compound IV, as illustrated in equation C below

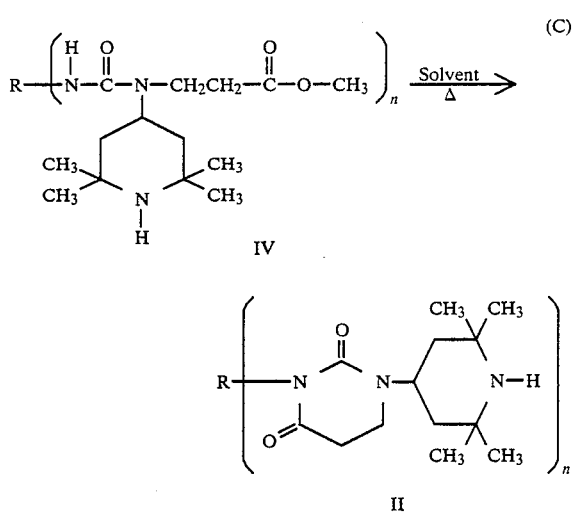

The urea is dissolved in a solvent, such as dimethylformamide, containing a small proportion of an alkaline compound such as sodium methylate, and the solution is refluxed for several hours, Thereafter, the solution is cooled, causing precipitation of the pyrimidinedione product, compound II. The precipitated solids are then separated by vacuum filtration, washed with solvent and air dried to yield a crude product.

The crude product so obtained, although it may be used as such, is preferably concentrated and purified. This can be normally achieved by recrystallization, using an appropriate solvent.

For practical reasons, the most preferred uracil derivatives of the invention are those which are derived from the reaction of N-(2,2,6,6-tetramethylpiperidin-4-yl)-amino-3-propionic acid methyl ester with a commercially available organic diisocyanate, $R(NCO)_2$, as illustrated in equation B above. The commercially available organic diisocyanates, and the corresponding identity of the R radical in the uracil compounds of the invention (formula II) are listed below

|     | Organic Diisocyanate | R Radical |
|-----|---------------------|-----------|
| (1) | ![tolylene diisocyanate structure] | tolylene |
| (2) | OCN—⟨C₆H₄⟩—CH₂—⟨C₆H₄⟩—NCO | 4,4'-diphenylmethane |
| (3) | ![1,5-naphthalene diisocyanate structure] | 1,5-naphthalene |
| (4) | OCN—CH₂—CH₂—CH₂—CH₂—CH₂—CH₂—NCO | 1,6-hexamethylene |

-continued

| | Organic Diisocyanate | R Radical |
|---|---|---|
| (5) | OCN—⟨cyclohexyl⟩—CH₂—⟨cyclohexyl⟩—NCO | 4,4'-dicyclohexylmethane |
| (6) | benzene ring with NCO (top), OCN (left), CH₃ (right), CH₃ (bottom) | 4,6-xylylene |
| (7) | cyclohexane with CH₃, CH₃ substituents, NCO and CH₂NCO, CH₃ | isophorone |
| (8) | OCN—CH₂—C(CH₃)(CH₃)—CH₂—CH(CH₃)—CH₂—CH₂—NCO | 2,2,4-trimethylhexamethylene |
| (9) | benzene with two NCO groups | phenylene |
| (10) | cyclohexane with two NCO groups | cyclohexylene |
| (11) | OCN—⟨C₆H₃(CH₃)⟩—CH₂—⟨C₆H₃(CH₃)⟩—NCO | 3,3'-dimethyldiphenylene |
| (12) | OCN—⟨C₆H₃(CH₃)⟩—CH₂—⟨C₆H₃(CH₃)⟩—NCO | 3,3'-dimethyldiphenylmethane |

The uracil derivatives of the invention, although non-polymeric, exhibit surprisingly high thermal stability. This is particularly the case with the preferred compounds of formula I in which n is 2. They are substantially inert, crystalline solids, light in color (i.e., white or near white) and compatible with various plastic media.

In accordance with the invention, it has been found that the uracil derivatives of the invention are effective as UV stabilizers in synthetic resins. By virtue of their surprisingly high thermal stability, they are particularly suited for use in those applications wherein a plastic material, be it thermoplastic or thermosetting, is subjected, during processing or use, to substantially elevated temperatures. Thus they can be used with all types of synthetic resins, illustrative of which are the polyolefins, polyamides, polyvinyl chloride, polyvinylidene chloride, polycarbonates, epoxy resins, ABS resins, polyaramides, polyhalcarbons, polyurethanes, etc. They are especially adapted for use as UV stabilizer additives in polyolefins, e.g. polypropylene and polyethylene.

When used to stabilize a plastic material against photodegradation, the uracil derivatives of the invention can be incorporated into the plastic in an amount or proportion which is effective for that purpose. Thus as used herein, the terms "effective amount" and "stabilizing amount" are intended to mean and include any such amount. Generally speaking, amounts varying from about 0.05 to about 2 percent by weight, based on the weight of the plastic, are sufficient, and in most instances a preferred range of about 0.1 to about 1 percent by weight is used.

The uracil compounds of the invention are incorporated into the synthetic resin by any suitable procedure. For example, conventional mixing equipment, such as a mill or Banbury mixer, may be used to blend the powdered uracil compound into the resin. If the resin has a melt viscosity which is too high for the desired use, the resin should be worked until its melt viscosity is brought down to the desired level before the addition of the uracil compound. Mixing is continued until the mixture is substantially uniform. It is preferable to also include in the resin mix an antioxidant such as octadecyl-3,5-ditertiarybutyl-4-hydroxyhydrocinnamate or 2,2'-methylene-bis(4-methyl-6-tertiarybutylphenol) terephthalate, both of which are commercially available materials. If desired, other additives may be incorporated into the resin which serve different functions. Illustrative are calcium stearate, which serves as a processing aid, sodium benzoate, which acts as nucleating or clarifying agent, pigments to add the desired color, and so forth.

The stabilized resin or polymer can be worked or processed into the desired shape by conventional methods such as milling, extruding, calendering, injection molding and the like.

The following examples are provided to illustrate the invention. In these examples, the test used to measure the thermal stability of various compounds is the so-called Thermo Gravimetric Analysis (hereinafter referred to as "TGA"). Briefly, a standard-size sample is heated at a pre-determined heating rate and its weight and rising temperature are constantly monitored during the heating process. A temperature vs weight graph is plotted, and for purposes of the examples, the temperature at which a 10% weight loss occurs (signifying initial break-down or loss of stability) is noted for each compound tested.

Further in the examples, the effectiveness of an additive as UV stabilizer is determined using a commercial accelerated weathering apparatus known as the Q(UV) panel in accordance with ASTM-G53-77 procedures. Briefly, a plastic specimen, in this case a 15 mil extruded film, is exposed to both UV radiation from fluorescent bulbs (16 hours at 60° C.) as well as water condensation (8 hours at 40° C.) from a heated reservoir. Subjective judgments of the progression of embrittlement, crazing, cracks, surface erosion and blooming are recorded and Hunter color measurements are taken. Failure occurs when a combination of these factors becomes excessive, and at this point, the number of days to failure is recorded.

Finally all parts and percentages given in the examples are by weight unless otherwise specified.

EXAMPLE 1

Preparation of
1,6-Hexamethylenebis-[3-(5,6-dihydro-2,4-pyrimidinedione-1-yl)-4-(2,2,6,6-tetramethyl-piperidine)]

A solution composed of 250.0 g of 4-amino-2,2,6,6-tetramethylpiperidine and 138.0 g of methyl acrylate in 1300 ml methanol was prepared then allowed to stand at room temperature (25° C.) for 48 hrs. The methanol was then removed by flash distillation on a rotary evaporator leaving a 383.0 g residue. This residue was identified by NMR and GC as being N-(2,2,6,6 Tetramethyl-piperidin-4yl)-amino-3-propionic acid methyl ester of 92.6% purity. This product is of sufficient purity to use for further reactions. Distillation of this product at reduced pressure through an 8" Vigreux column and collecting the fraction boiling from 98° to 105° C. at 0.3 mm Hg gave 300.0 g of product having the following elemental analysis:

Carbon: 64.38% found (versus 64.47% calculated)
Hydrogen: 10.77% found (versus 10.74% calculated)
Nitrogen: 11.22% found (versus 11.57% calculated)

A gas chromatograph of the distillate found it to be of 99.1% purity.

A solution of 101 g of 1,6 Diisocyanato-hexane in 200 ml of ethyl ether was added over a period of 30 min. to a stirred solution of 290.4 g N-(2,2,6,6-Tetramethylpiperidin-4-yl)-amino-3-propionic acid methyl ester in 100 ml ethyl ether. The temperature was maintained at 25° C. throughout the addition by means of an ice bath.

After the addition was complete the mixture was allowed to stir for 1 hr. at 25° C. and then refluxed for 1½ hrs. The white solids which formed were separated by filtration, washed with ether and dried in a vacuum oven at 60° C. and 15 mm pressure. The yield of this intermediate bis urea was 352 g (90%) and its structure was confirmed by NMR. Its elemental analysis was as follows:

Carbon: 62.63% found (versus 62.58% calculated)
Hydrogen: 9.82% found (versus 9.82% calculated)
Nitrogen: 12.75% found (versus 12.88% calculated)

A 62.0 g portion of this intermediate bis urea was dissolved in 90 ml dimethylformamide containing 0.47 g sodium methylate and the solution refluxed for 3 hrs. Cooling of the solution caused white solids to be deposited. These solids were separated by vacuum filtration, washed with ether, and air dried to give 41.6 g (74.4%) of crude bis uracil. Recrystallization from isopropyl alcohol gave and 33.5 g (60%) of white crystals confirmed by NMR as the title product and having a melting point of 162° C. The elemental analysis was as follows: Calculated (Found)

C-65.31 (64.84); H-9.52(9.27); N-14.28(13.84)

EXAMPLE 2

Preparation of
1,1'-Methylenebis-[4-phenylene-3-(5,6-dihydro-2,4-pyrimidinedione-1-yl)-4-(2,2,6,6-tetramethyl-piperidine)]

A solution of 37.3 g 4,4'diphenyl-methane diisocyanate in 445 ml of methylene chloride was added over 15 min. period at 25° to 35° C. to a stirred solution of 72.0 g N-(2,2,6,6-Tetramethylpiperidin-4-yl)-amino-3-propionic acid methyl ester, prepared as shown in Example 1, in 295 ml methylene chloride. After the addition was complete the solution was refluxed for 1 hr., cooled to 25° C. filtered free of solids and the filtrate stripped of volatiles on a rotary evaporator. The semi-solid residue was dissolved in refluxing isopropyl alcohol and water was added to the refluxing solution until a slight turbidity was observed. Continued refluxing over a 15 min. period caused the precipitation of white solids which after cooling to 25° C. were removed by filtration and washed with a 50:50 mixture of isopropanol and water. These still damp solids were then recrystallized from ethanol to give 60 g (56%) of the title product whose structure was confirmed by mass spec. and NMR. m.p. 280° C. Elemental analysis Calculated (Found):

C-69.82(68.08); H-8.11(7.89); N-12.53(11.41)

Thermal Stability and UV Stabilizer Tests

The TGA thermal stability of each of the compounds prepared in Examples 1 and 2 was measured along with those of two commercially available, polymeric UV stabilizers. The latter are identified by the trademarks Chimassorb-944LD and Cyasorb-UV 3346. The results are shown in Table I below.

The effectiveness of each of the four compounds (i.e., the two compounds obtained in Examples 1 and 2, and the two polymeric, commercial products) as UV stabilizers in plastics was determined. The plastic used was powdered polypropylene. In each case, a sample containing 0.25% of each stabilizer and 0.05% of a commercial antioxidant available under the trademark Irganox 1076 was extruded at elevated temperature into a 15 ml film. A specimen film was then tested using a Q(UV) panel in accordance with ASTM-G53-77 as briefly summarized above. A control specimen containing no UV stabilizer additive was also tested in the same manner. The results are provided in Table I below.

The data is Table I demonstrates that although color change is negligible in the case of each polypropylene sample including the sample containing no stabilizer at all, the stabilizing effect of two uracil derivatives of the invention (as measured by the number of days to failure) is comparable to that of the two prior art stabilizers. Moreover, the data shows that although the uracil compounds of the invention are monomeric, they exhibit substantially comparable thermal stability attributes as those of the polymeric, prior art materials.

TABLE I

| UVLS Additive | M.P. (°C.) | TGA, Temp, °C. @ 10% Wt. Loss | Days to Failure | Hunter color, Initial | Final |
| --- | --- | --- | --- | --- | --- |
| EXAMPLE 1 | 170-175 | 310 | >35 | −0.99 | −0.22 |
| EXAMPLE 2 | 278-281 | 360 | 28 | −0.97 | 2.05 |
| Chimassorb-944LD (CIBA GEIGY) | 296 | 375 | 28 | −0.97 | −0.93 |
| Cyasorb-UV 3346 (American Cyanamid) | 110-130 | 340 | 35 | −0.85 | −0.47 |
| Blank | — | — | 14 | 1.07 | 0.12 |

EXAMPLES 3-4

The other uracil derivatives of the invention were prepared using essentially the same procedure as that of Example 2 except for the fact that instead of 4,4'-diphenylmethane diisocyanate, other organic diisocyanates were used, namely, 2,4-toluene diisocyanate was used in Example 3 and p-phenylene diisocyanate was used in Example 4. The melting point and TGA thermal stability of the resulting compounds is provided in Table II below.

EXAMPLES 5-9

To illustrate the preparation of compounds of formula I wherein n is 1, the procedure of Example 1 was followed except that in each of Examples 5-9 a monoisocyanate was used instead of diisocyanate. Based on the particular isocyanate reactant used in each example, the R radical in the final product is identified in Table II together with the melting points and TGA thermal stabilities of the resulting compounds.

TABLE II

| EXAMPLE OR COMPARISON | R | n | M.P. (°C.) | TGA (°C.) @ 10% Wt. Loss |
| --- | --- | --- | --- | --- |
| E-3 | tolulene | 2 | 267 | 365 |
| E-4 | phenylene | 2 | 340 | 320 |
| E-5 | methyl | 1 | 124 | 210 |
| E-6 | cyclohexyl | 1 | 123 | 220 |
| E-7 | phenyl | 1 | 209 | 245 |
| E-8 | p-chlorophenyl | 1 | 167 | 270 |
| E-9 | benzyl | 1 | 156 | 235 |

EXAMPLE 10

Preparation and Testing of a Typical Mono-Uracil (a) Preparation of 1-(2,2,6,6-Tetramethyl piperidin-4-yl)-3-(1-chloro-4-phenylene)-5,6-dihydro-2,4-pyrimidinedione A solution of 34.0 g (0.221 m) of p-chlorophenyl isocyanate in 75 ml dimethylformamide was added over a 15 minute period to a stirred solution of 53.5 g (0.221 m) of N-(2,2,6,6-tetramethylpiperidin-4-yl)-amino-3-propionic acid methyl ester in 85 ml dimthylformamide maintained at 25° to 30° C. by means of an ice bath. The mixture was then heated by an oil bath to 153° C. and maintained at this temperature for one hour. The dimethylformamide was then removed from the mixture by means of a rotary evaporator leaving an oil which crystallized on standing. These solids were recrystallized from isopropyl alcohol to give 29.5 g (36.7 percent) of white solids having a melting point of 167° C. These crystals were subject to NMR spectroscopy which confirmed them to be the title product. The elemental analysis of the product was as follows:

Carbon: 62.63% found (versus 62.72 calculated)
Hydrogen: 7.43% found (versus 7.20 calculated)
Nitrogen: 11.12% found (versus 11.55 calculated)
Chlorine: 9.94% found (versus 9.74 calculated)

(b) Testing the Title Compound

The TGA at a 10 percent weight loss is noted in Table II above (refer to E-8) as being 270° C. When tested for UV stabilizer properties in polypropylene using the procedure as described above with respect to Examples 1 and 2, the title product failed after 14 days, as compared to a blank which failed after 6 days. The title compound exhibited color change during this test failing within an acceptable range.

By analogous testing of the other products referred to as E-3 to E-7 and E-9 of Table II, E-6 was determined to be the preferred mono-uracil product.

What is claimed is:

1. A synthetic resin composition which is stabilized against the degradative effect of ultraviolet light by the presence therein of a stabilizing amount of a uracil derivative having the formula

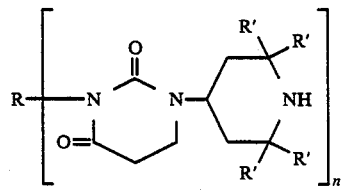

wherein each R' is independently an alkyl radical, n is 1 or 2, and R is a substituted or unsubstituted aliphatic radical, cycloaliphatic radical, aromatic radical or aromatic-aliphatic radical.

2. The composition of claim 1 wherein said synthetic resin is a polyolefin.

3. The composition of claim 2 wherein said polyolefin is polypropylene.

4. The composition of claim 1 wherein R is selected from the group consisting of alkylene having 1 to 12 carbon atoms, cycloalkylene having 5 to 20 carbon atoms, arylene having 6 or 12 ring carbon atoms, aralkylene having 7 to 20 carbon atoms, alkarylene having 7 to 20 carbon atoms.

5. The composition of claim 1 wherein R is selected from the group consisting of alkylene having 3 to 10 carbon atoms, cycloalkylene having 6 to 15 carbon atoms, arylene having 6 or 12 ring carbon atoms, and aralkylene having 7 to 16 carbon atoms.

6. The composition of claim 1 wherein n is 1 and R is selected from the group consisting of phenyl; p-chlorophenyl; methyl; cyclohexyl; and benzyl.

7. The composition of claim 1 wherein n is 2 and R is selected from the group consisting of tolylene; 4-4'-diphenylmethane; 1,5-naphthalene; 1.6-hexamethylene; 4,4'-dicyclohexylmethane; 4,6-xylylene; isophorone; 2,2,4-trimethylhexamethylene; phenylene; cyclohexylene; 3,3'-dimethyldiphenylene; and 3,3'-dimethyldiphenylmethane.

8. The composition of claim 1 wherein R' is methyl.

9. A method of stabilizing a synthetic resin composition against photodegradation which comprises incorporating into said composition a stabilizing amount of the uracil derivative recited in claim 1.

10. A method of stabilizing a synthetic resin composition against photodegradation which comprises incorporating into said domposition a stabilizing amount of the uracil derivative according to claim 4.

11. A method of stabilizing a synthetic resin composition against photodegradation which comprises incorporating into said composition a stabilizing amount of the uracil derivative according to claim 5.

12. A method of stabilizing a synthetic resin composition against photodegradation which comprises incorporating into said composition a stabilizing amount of the uracil derivative according to claim 6.

13. A method of stabilizing a synthetic resin composition against photodegradation which comprises incorporating into said composition a stabilizing amount of the uracil derivative according to claim 7.

14. A method of stabilizing a synthetic resin composition against photodegradation which comprises incorporating into said composition a stabilizing amount of the uracil derivative according to claim 8.

* * * * *